United States Patent
Brajtling

(10) Patent No.: US 10,835,632 B2
(45) Date of Patent: Nov. 17, 2020

(54) AUTOCLAVE FOR THE PROCESSING OF MUNICIPAL WASTE

(71) Applicant: BIOELEKTRA GROUP S.A., Warsaw (PL)

(72) Inventor: Eryk Jaroslaw Brajtling, Szcecin (PL)

(73) Assignee: BIOELEKTRA GROUP S.A., Warsaw (PL)

( * ) Notice: Subject to any disclaimer, the term of this patent is extended or adjusted under 35 U.S.C. 154(b) by 0 days.

(21) Appl. No.: 16/344,465

(22) PCT Filed: Dec. 6, 2016

(86) PCT No.: PCT/PL2016/000144
§ 371 (c)(1),
(2) Date: Apr. 24, 2019

(87) PCT Pub. No.: WO2018/080327
PCT Pub. Date: May 3, 2018

(65) Prior Publication Data
US 2019/0328925 A1    Oct. 31, 2019

(30) Foreign Application Priority Data
Oct. 28, 2016    (PL) .......................................... 419294

(51) Int. Cl.
*A61L 11/00*    (2006.01)
*B09B 3/00*    (2006.01)

(52) U.S. Cl.
CPC ............ *A61L 11/00* (2013.01); *B09B 3/0083* (2013.01); *A61L 2202/122* (2013.01)

(58) Field of Classification Search
None
See application file for complete search history.

(56) References Cited

U.S. PATENT DOCUMENTS 4,974,781 A * 12/1990 Placzek ..................... B03B 1/00
241/17
6,752,956 B1 * 6/2004 Vanderwal .............. A61L 11/00
422/3

(Continued)

FOREIGN PATENT DOCUMENTS

GB    2472599 A    2/2011

OTHER PUBLICATIONS

International Search Report of the European Patent Office received for Application No. PCT/PL2016/000144, dated Jun. 21, 2017, 2 pages.

*Primary Examiner* — Jelitza M Perez
(74) *Attorney, Agent, or Firm* — Ziegler IP Law Group, LLC

(57) ABSTRACT

An autoclave with an upper hatch and a bottom hatch is terminated with elliptical end caps has an agitator placed inside it. The autoclave is inclined in relation to the ground plane. An external jacket is mounted on the cylindrical section of the internal pressure chamber. The jacket is divided into pressure-separated parts Inside the internal pressure chamber a paddle agitator shaft is mounted. The agitator mounting arrangement is out-of-alignment in relation to the axis of symmetry of the autoclave cylindrical section The size of the shift does not exceed ⅔ of the radial length of the cross-section of the cylindrical section of the internal pressure chamber. The agitator's paddles has two shields shifted in the agitator's axis of symmetry in relation to its paddle by a phase angle equal to 90°. The shield height does not exceed ⅓ of the height of the agitator's paddle.

4 Claims, 2 Drawing Sheets

(56) References Cited

U.S. PATENT DOCUMENTS

2011/0121112 A1 5/2011 Alford
2011/0185624 A1 8/2011 Hall

* cited by examiner

A − A

AUTOCLAVE FOR THE PROCESSING OF MUNICIPAL WASTE

FIELD

The aspects of the disclosed embodiments relate to an autoclave for the processing of municipal waste or fractions of municipal waste, particularly biodegradable organic fractions contained in mixed municipal waste. The invention finds applications mainly in waste sterilization, mixed municipal waste management and obtaining biomass with high functional properties, as well as recovery of secondary raw materials.

BACKGROUND

In an age of dynamic economic development, mixed municipal waste generated by communities all over the world prompted engineers to search for various solutions and methods for waste management.

Currently, several methods exist for the recovery of raw materials from mixed municipal waste. Some of them lead directly to the recovery of materials intended for recycling in various industries, while others utilise thermal methods for the recovery of energy, as well as biogas installations at landfills.

One of the methods for the recovery of materials intended for recycling consists in a process carried out in installations operating at ambient temperature and atmospheric pressure, by use of the mechanical and pneumatic classification of mixed municipal waste. However, some exceptions while using of this method are known, which consist in increasing the temperature to about 50° C.-60° C., while maintaining atmospheric pressure. Nonetheless, both variants of this method are oriented toward the recovery of secondary raw materials such as various kinds of plastics (non-biodegradable organic fraction), metals, glass and paper. Percentages of these raw materials in the average composition of mixed household municipal waste amount to about 34% by wt. having a total content of bound moisture of 77%, giving 34 kg of raw materials per 100 kg of mixed municipal waste. After the completion of mechanical processing by the aforementioned methods and stabilisation of the bound moisture level, resulting from the natural drying process, the recovery level amounts to 14% by wt. with a total content of bound moisture of approximately 20%, giving 10 kg of raw materials per 100 kg of mixed municipal waste.

The rest of the waste, that is about 66%, is disposed in landfills for municipal waste. This amount includes the compost fraction (biodegradable fraction), the fraction highly polluted with mineral and plastics and foil elements, as well as in the form of so-called stabilized compost.

In another method, procedures for the transformation of waste into electrical or thermal energy are used. They allow for obtaining a product having the form of energy from mixed municipal waste. Frequently, they are carried out in combination with mechanical and pneumatic methods for waste segregation. The thermal methods used include direct methods, consisting in waste incineration at high temperatures in waste incineration plants or gasification, and indirect methods, comprising aerobic or anaerobic fermentations aimed at the production of combustible gas, as well as the formation of an alternative fuel from municipal waste.

Yet another method utilizes biogas generation plants at municipal waste landfills, based on the natural phenomenon of the liberation of a gaseous mixture with a high content of methane and other combustible gases.

All the aforementioned methods, leading to the generation of various raw materials and products, enable only partial waste management. The majority of these methods, in spite of the application various modern technical solutions, generate other waste and side effects.

An important issue connected with municipal waste processing is their disagreeable odour. This odour is noticeable at all stages of waste recovery and classification.

Inasmuch as the waste classification is carried out on the material originating directly from landfills, this odour, resulting from the occurring digestion processes, causes an important nuisance for both personnel and local residents.

Methods for waste sanitisation are known. They consist in the treatment of waste with hot steam. Admittedly, the odour of the waste is eliminated, but the obtained waste water with an intense disagreeable odour remains an obtrusive side effect. Moreover, the waste requires further complicated drying.

Currently, a compatible mounting of the rotating shaft axis, i.e. coaxial with the geometry of the central axis of the autoclave internal chamber, is used in chambers of mixers and stationary autoclaves having a cylindrical form. Such a way of mounting the shaft, on which various agitators are installed, limits the possibilities to mix non-homogeneous mixtures simultaneously in one chamber in the context of materials of various sizes and physico-chemical properties. Irrespective of the agitator design, numerous contact points between the agitator structure and the surface of the internal cladding occurs then. Such a solution results in material jamming in the agitator-cladding contact zone, causing mixer blocking.

Additionally, in mixers and autoclaves used presently for biomass processing, mixers with an exposed agitator shaft or a coil wound onto the shaft are utilised. Such a construction leads to the winding of textiles and foils around the shaft, resulting in a frequent need for shaft cleaning or a damage to the shaft or the agitators.

U.S. Pat. No. 6,752,956 discloses a horizontal autoclave for waste processing. The autoclave is equipped with an agitator installed at the axis of a symmetrical reactor. The agitator has cutting edges on the ends of its blades, breaking up the waste into small elements. The cutting edges are intended for the prevention of the winding of waste around the agitator shaft. However, before the waste can be cut, a part of it is wound around the agitator shaft. Moreover, such high break-up of the waste precludes its further classification, and therefore the waste should be segregated before its processing in the autoclave. The autoclave has a heating jacket fed with hot water or steam. This jacket is a single-zone jacket, so there is no possibility to adjust the temperature in various areas of the autoclave interior. Another disadvantage consists in the horizontal positioning of the autoclave. The agitator only moves the waste upwards and downwards, without transporting it along the autoclave axis. This results from the lack of such a need, as analogous conditions prevail in the whole autoclave. Moreover, the agitator is always rotated in the same direction, precluding liberation of the waste blocked between the agitator blades and the autoclave wall.

SUMMARY

The aspects of the disclosed embodiments include a pressure autoclave for periodical operation in the form of a cylinder, having an upper hatch for waste loading and a bottom hatch for receiving the processed waste, terminated with elliptical end caps on both sides. The autoclave is inclined in relation to the ground plane by an angle of 3-8 degrees towards its outlet. An external jacket in the form of a membrane forming an external pressure space is mounted on the cylindrical section of the chamber. The external jacket constitutes a heating space for the internal pressure chamber of the autoclave. Through the external jacket steam flows, which during its flow gives up thermal energy to the interior of the internal pressure chamber of the autoclave, heating the charge located inside. The external jacket is divided into at least two parts, preferably three parts, pressure-separated, preferably placed symmetrically along the cylindrical section of the autoclave. Separation of the external pressure subspaces in the external jacket enables a precise adjustment of the heating steam flow on the whole surface of the autoclave with a precision depending on the partitioning of the external jacket. This results in precise control over the heat exchange between the external space and the interior of the autoclave.

Heat exchange parameters, temperature and pressure in the external pressure spaces are monitored by measurement devices located in measurement stub pipes, separately for every space, connected mechanically only with the external spaces.

Monitoring of heat exchange parameters, temperature and pressure in the autoclave is carried out using measurement devices located in measurement stub pipes connected mechanically only with the internal pressure chamber of the autoclave.

Additionally, it is possible for the steam to be fed into the interior of the autoclave by a stub pipe connected mechanically only with the internal pressure chamber of the autoclave and the atmosphere, and to carry out the steam offtake from the interior of this chamber by the same or another stub pipe connected mechanically only with the internal pressure chamber of the autoclave. A paddle agitator shaft is mounted inside the pressure chamber of the autoclave. The agitator can perform a clockwise rotation and a counter-clockwise rotation. The agitator mounting arrangement is out-of-alignment in relation to the axis of symmetry of the autoclave's cylindrical section. Separation of the geometrical axis of the agitator shaft and that of the autoclave's cylindrical section is done by a shift of the mounting of the geometrical axis of the agitator shaft along the y-axis in a planar geometrical system. The planar geometrical system is circumscribed on a cross-section of the internal pressure chamber of the autoclave and the agitator. The size of the shift does not exceed ⅔ of the radial length of the cross-section of the cylindrical section of the autoclave chamber.

The geometry of the agitator shaft enables installation of a lateral shaft shield along the shaft, preferably in the form of sheet plates. Each of the agitator paddles has two shields, one for each of the opposite sides of the paddle. Each of the shields is shifted in the agitator's axis of symmetry by a phase angle equal to 90° in relation to its paddle. The shield height does not exceed ⅓ of the height of the agitator's paddle.

In the so-constructed mechanical system, mechanical-heat treatment and sterilisation are carried out according to the description. A pressure between 1 and 5 bar and a temperature in the range of 100°-154° C. are maintained in the autoclave pressure chamber, and the retention time of the waste in the autoclave is from 45 min to 240 min. The above parameters are monitored during the process.

As a result of the application of such conditions of the process, all substances included in the morphological composition of mixed municipal waste are subjected to sterilisation. The matter becomes sterile from the bacteriological and virological point of view, leading to its hygienisation and elimination of digestion and fermentation processes. Under such conditions, biodegradable organic substances undergo defibration. The use of water and steam creates conditions for the denaturation of proteins, resulting in the isolation of fibres. Water and steam accelerate and facilitate processes of hydrolytic decomposition of biodegradable organic substances to more simple fragments. Simultaneously, the process conditions applied prevent or hinder the occurrence of reactions with the liberation of gaseous substances or other substances volatile at such temperatures. Additionally, a cyclic change in the direction of the agitator's rotation facilitates mixing of the charge and prevents its blocking or winding around the shaft. Water contained in municipal waste is a sterilising agent, and bound water evaporating from the biodegradable organic fraction changes its structure and causes its fibration. Moreover, due to the inclination of the autoclave towards its outlet and to the division of the heating jacket into separate sections, the waste bulk moves in the autoclave and it may be subjected to variable temperature conditions.

After completion of the process, pressure and temperature stabilisation occurs in the conditions of atmospheric pressure and ambient temperature. The system is decompressed until the pressure in the interior equalises with atmospheric pressure. The system is depressurised, and the processed waste is unloaded from the pressure chamber of the autoclave.

The so-processed waste (mixed municipal waste and/or waste fractions) is ready to be classified into fractions on mechanical, pneumatic and optoelectronic sorters.

The obtained biomass has a loose form and is devoid of the odour of mixed municipal waste. The biomass obtained by the method according to the invention is suitable for use as an energy carrier or/and a soil improver. The rest of the secondary raw materials is suitable for segregation without liberating the disagreeable odour of mixed municipal waste to the environment, as well as without the necessity of drying.

BRIEF DESCRIPTION OF FIGURES

The aspects of the disclosed embodiments are illustrated in the drawings, wherein.

DETAILED DESCRIPTION OF THE EMBODIMENTS

Figure 1:
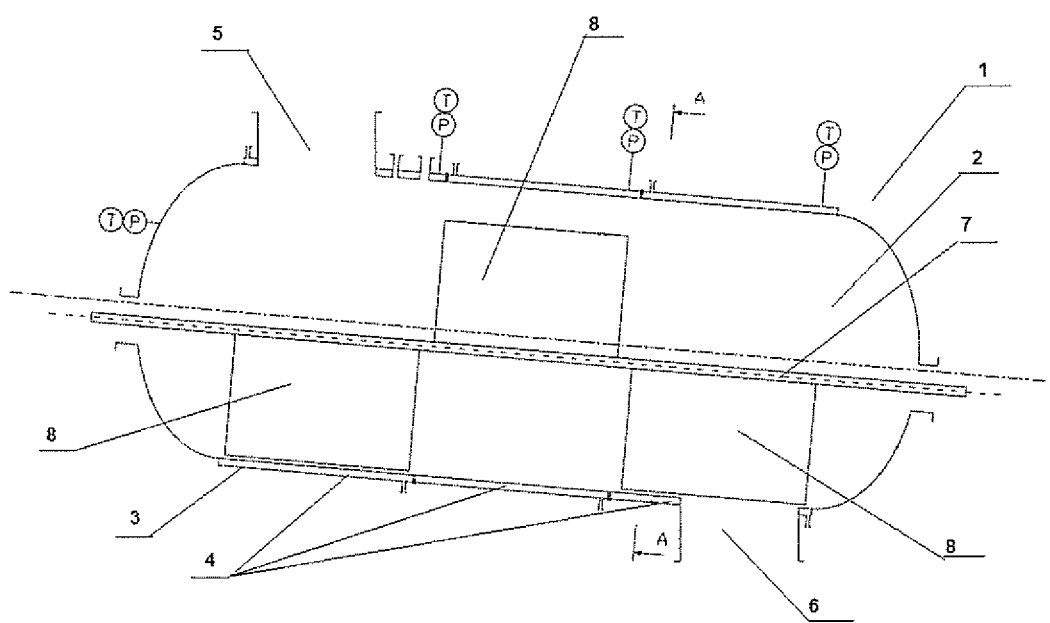
FIG. 1 is a longitudinal section of the autoclave with the agitator's paddles shown and with the shields not shown (in order to facilitate the clarity of the drawing)
Figure 2:
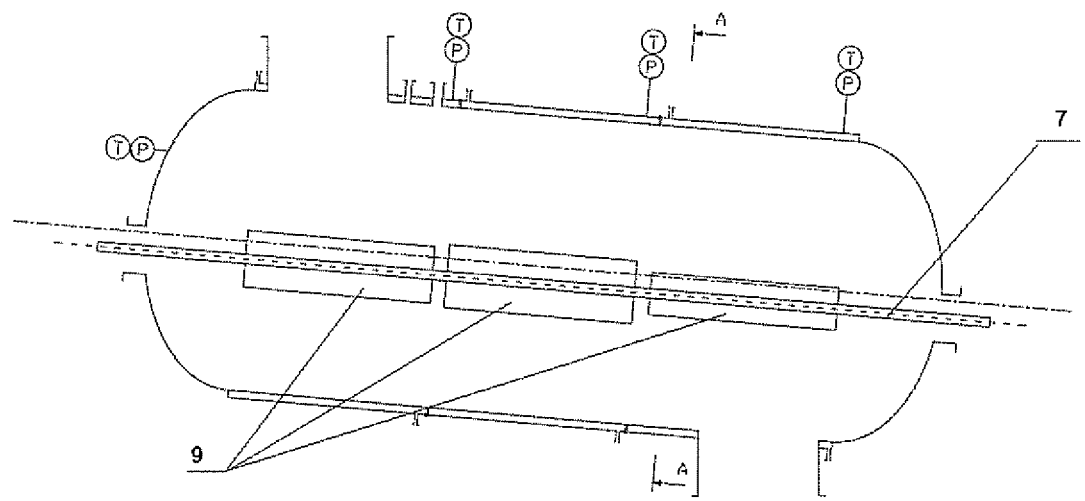
FIG. 2 is a longitudinal section of the autoclave with the shields shown and with the agitator's paddles not shown (in order to facilitate the clarity of the drawing)
Figure 3:
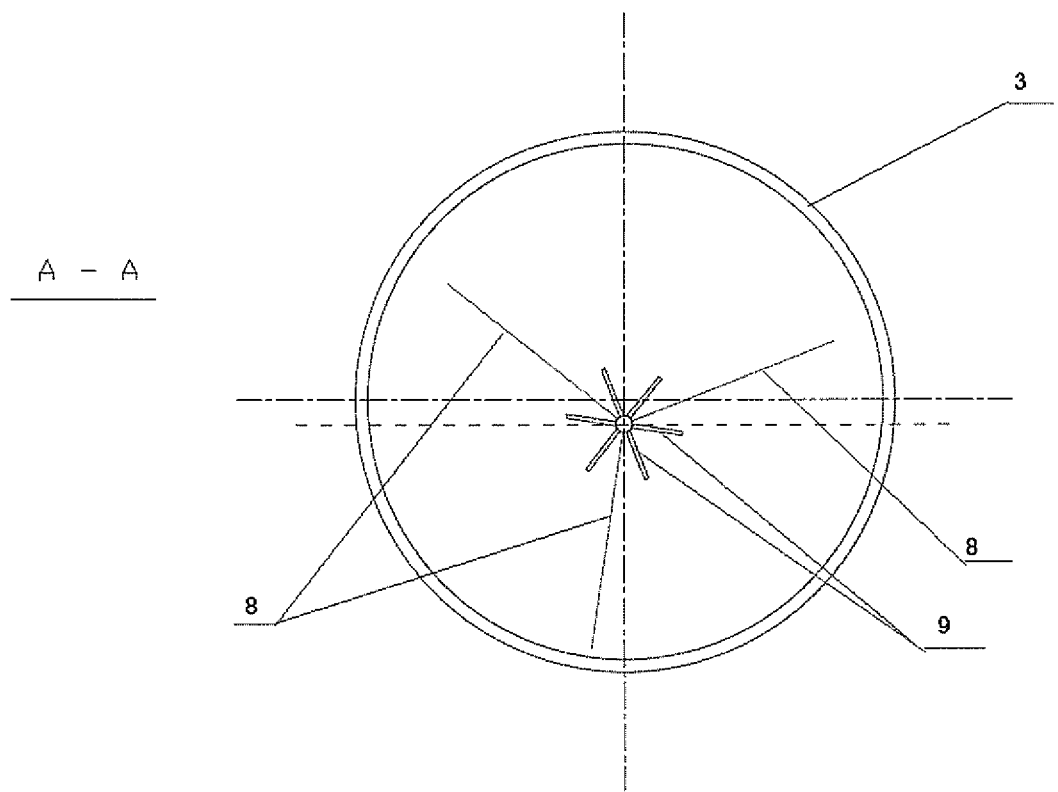
FIG. 3 shows a cross-section of the autoclave along the A-A line with the agitator's paddles and the shields both shown.

An embodiment of the autoclave for the processing of municipal waste or fractions of municipal waste consists in an autoclave 1 in the form of a cylinder having an upper hatch 5 and a bottom hatch 6, and terminated with elliptical end caps on both sides. The autoclave 1 is inclined in relation to the ground plane by an angle of 7° towards its outlet. An agitator is mounted inside the internal pressure chamber 2 of the autoclave 1. The agitator is capable of changing the direction of its rotation cyclically between the clockwise rotation and the counter clockwise rotation. The agitator is mounted in necks projecting from two elliptical end caps. The geometrical axis of the agitator's shaft 7 is separated from the geometrical axis of the cylindrical section of the internal pressure chamber 2 of the autoclave 1 by a shift of the mounting of the geometrical axis of the agitator's shaft 7 by ⅔ of the radial length of the cross-section of the cylindrical section pressure chamber 2 of the autoclave 1 along the y-axis. Three paddles 8 are installed on the shaft 7, and each of them is equipped with two shields 9. Each of the latter is shifted in the agitator's axis of symmetry by a phase angle equal to 90° in relation to its paddle 8. The shield 9 height amounts to ⅓ of the height of the agitator's paddle 8.

An external jacket 3 in the form of a membrane forming an external pressure space is mounted on the cylindrical section of the internal pressure chamber 2 of the autoclave 1. The external pressure space is divided into two pressure-separated parts 4, placed symmetrically along the cylindrical section of the internal pressure chamber 2 of the autoclave 1. Each of the separated pressure spaces 4 contains measurement devices placed in measurement stub pipes, which also serve the purpose of feeding the steam for each space 4 separately. The internal pressure chamber 2 of the autoclave 1 has its own measurement stub pipes with measurement devices T and P for the monitoring of parameters of heat exchange, temperature and pressure. The steam is fed into the interior of every section of the pressure space 4 by a stub pipe connected mechanically with the pressure space 4 and the atmosphere. The steam offtake from the interior of the pressure space is performed by the same or another stub pipe connected mechanically only with the pressure space 4.

Mixed municipal waste (the charge) with the following morphological composition:

| | |
|---|---|
| Fraction of <10 mm | 8% |
| Fraction of 10-20 mm | 18% |
| Wood | 1% |
| Paper and cardboard | 17% |
| Plastics | 15% |
| Textiles | 4% |
| Metals | 2% |
| Multicomponent waste, including hygienic waste | 6% |
| Bulky waste | 4% | is subjected to homogenisation on a pre-shredder until a grain size lower than 800 mm is obtained. Then it is loaded into the internal pressure chamber 2 of the autoclave 1, until the volume of the pressure chamber 2 of the autoclave 1 is 55% filled. The loading is carried out using the upper hatch 5. When the charge volume of 55% (corresponding to a charge of 3200 kg) is reached, the upper hatch 5 is sealed. Measurement of the loaded mass is carried out on the charge feeder using conveyor scales.

During both loading and mechanical-heat processing, the external jacket 3 is heated to a temperature of 165° C. and the pressure is increased to 6.2 bar using saturated steam. The external jacket 3 temperature is monitored by thermometers installed on it, and the pressure is monitored by manometers installed on it. Inside the internal pressure chamber 2 of the autoclave 1, the agitator operates, performing an alternating clockwise/counter-clockwise rotation, carrying out the process of the charge mixing. The steam flowing through the external jacket 3 gives up its heat energy to the charge located in the internal pressure chamber 2 of the autoclave 1, heating it to a temperature of 130° C. and increasing the pressure to 3 bar. The temperature in the internal pressure chamber 2 of the autoclave 1 is monitored on thermometers T installed on it, and the pressure is monitored by manometers P installed on it. Reaching the temperature of 130° C. and the pressure of 3 bar lasts 60 min. The charge is maintained at this temperature and under this pressure for the next 80 min. After this time is measured by a clock, the process of pressure equalisation in the interior with atmospheric pressure takes place by opening of the outlet of the steam offtake pipe stub. The process pressure equalisation in the internal pressure chamber 2 of the autoclave 1 with atmospheric pressure is observed on a manometer P installed in the internal chamber space. After reaching atmospheric pressure in the internal pressure chamber 2 of the autoclave 1, the upper hatch 5 is opened and then the bottom hatch 6 is opened, and the charge is unloaded via the bottom hatch 6 onto a feeder which transports the charge to the sorting line.

The obtained biomass had a loose form and is devoid of the odour of mixed municipal waste. The biomass obtained by the method according to the invention is suitable for use as an energy carrier or/and a soil improver. The rest of the secondary raw materials is suitable for segregation without liberating the disagreeable odour of mixed municipal waste to the environment, as well as without the necessity of drying.

The invention claimed is:

1. An autoclave for processing municipal waste or fractions of municipal waste, particularly biodegradable organic fractions contained in mixed municipal waste, the autoclave having a form of a cylinder with an upper hatch and a bottom hatch, terminated with elliptical end caps on both sides, and having an agitator placed inside the autoclave and mounted in necks projecting from the elliptical end caps,
    wherein the autoclave is inclined in relation to a ground plane by an angle of 3-8 degrees towards an outlet of the autoclave,
    an external jacket in a form of a membrane forming an external pressure space is mounted on a cylindrical section of an internal pressure chamber of the autoclave; the external pressure space being divided into at least two pressure-separated parts,
    wherein the agitator is mounted inside the internal pressure chamber and is configured to perform a clockwise rotation and a counter-clockwise rotation,
    a shaft of the agitator is disposed out-of-alignment in relation to an axis of symmetry of the cylindrical section by a shift of a mounting of a geometrical axis of the shaft along a y-axis in a planar geometrical system, and wherein a size of the shift does not exceed ⅔ of a radial length of a cross-section of the cylindrical section,
    wherein the shaft comprises a paddle, and the paddle further comprises two shields, one shield being disposed on one side of the paddle and another shield being disposed on an other side of the paddle,
    each of the two shields is shifted in an axis of symmetry of the of the agitator in relation to the paddle by a phase angle equal to 90°, and
    wherein a height of at least one of the two shields does not exceed ⅓ of a height of the paddle.

2. The autoclave according to claim 1, wherein the external jacket is divided into three pressure-separated parts placed symmetrically along the cylindrical section of the autoclave.

3. The autoclave according to claim 1, wherein the paddle is made of a sheet plate.

4. The autoclave according to claim 3, wherein the shaft includes three paddles.

\* \* \* \* \*